(12) United States Patent
Coene et al.

(10) Patent No.: US 8,520,212 B2
(45) Date of Patent: Aug. 27, 2013

(54) SCATTEROMETRY METHOD AND MEASUREMENT SYSTEM FOR LITHOGRAPHY

(75) Inventors: Willem Marie Julia Marcel Coene, Geldrop (NL); Hugo Augustinus Joseph Cramer, Eindhoven (NL); Irwan Dani Setija, Utrecht (NL)

(73) Assignee: ASML Netherlands B.V., Veldhoven (NL)

( * ) Notice: Subject to any disclaimer, the term of this patent is extended or adjusted under 35 U.S.C. 154(b) by 162 days.

(21) Appl. No.: 13/000,212

(22) PCT Filed: Jul. 10, 2009

(86) PCT No.: PCT/EP2009/058862
§ 371 (c)(1),
(2), (4) Date: Mar. 24, 2011

(87) PCT Pub. No.: WO2010/007010
PCT Pub. Date: Jan. 21, 2010

(65) Prior Publication Data
US 2011/0304851 A1    Dec. 15, 2011

Related U.S. Application Data

(60) Provisional application No. 61/081,890, filed on Jul. 18, 2008.

(51) Int. Cl.
*G01N 21/55* (2006.01)
(52) U.S. Cl.
CPC .................................... *G01N 21/55* (2013.01)
USPC ........................................................ 356/445
(58) Field of Classification Search
CPC .................................................... G01N 21/55

USPC ................................................. 356/445–448
See application file for complete search history.

(56) References Cited

U.S. PATENT DOCUMENTS

2006/0172447 A1    8/2006 Do et al.
2007/0229854 A1    10/2007 Wu et al.

FOREIGN PATENT DOCUMENTS

EP            1 628 164 A2    2/2006

OTHER PUBLICATIONS

International Preliminary Report on Patentability and Written Opinion directed to related International Application No. PCT/EP2009/058862, mailed on Jan. 27, 2011, The International Bureau of WIPO, Geneva, Switzerland; 9 pages.
International Search Report directed to related International Patent Application No. PCT/EP2009/058862, mailed Sep. 9, 2009; 2 pages.

*Primary Examiner* — Michael P Stafira
(74) *Attorney, Agent, or Firm* — Sterne, Kessler, Goldstein & Fox P.L.L.C.

(57) ABSTRACT

Scatterometry method and apparatus are useful in a lithographic apparatus and device manufacturing. A back focal plane diffraction intensity image of a measurement projection system configured to project a radiation beam onto a target portion of a substrate is measured. A beam of radiation having a first wavelength is directed to the substrate. A diffraction image of a zeroth diffraction order and higher order diffraction from a diffraction structure in the substrate is provided. A first layer (4) of the diffractionstructure provides a diffraction image having only a zeroth diffraction order. A second layer (5) has a periodic structure (6a, 6b) configured such that a lowest spatial frequency of the periodic structure is lower than spatial frequencies of interest of the first structure. From the diffraction image originating from diffraction of the radiation beam in both the first and second layer a critical dimension metrology parameter is determined.

20 Claims, 3 Drawing Sheets

SCATTEROMETRY METHOD AND MEASUREMENT SYSTEM FOR LITHOGRAPHY

CROSS-REFERENCE TO RELATED APPLICATIONS

This application claims the benefit of U.S. provisional application 61/081,890, which was filed on Jul. 18, 2008, and which is incorporated herein in its entirety by reference.

BACKGROUND

1. Field of the Invention

The present invention relates in general to a lithographic apparatus and a method of manufacture of a device using lithographic apparatus. More specifically, the invention relates to a scatterometry method measuring a back focal plane diffraction intensity image and a measurement system.

2. Background Art

A lithographic apparatus applies a desired pattern onto a substrate, usually onto a target portion of the substrate. A lithographic apparatus can be used, for example, in the manufacture of integrated circuits (ICs). A patterning device, which is alternatively referred to as a mask or a reticle, may be used to generate a circuit pattern to be formed on an individual layer of the IC. This pattern can be transferred onto a target portion (e.g., comprising part of, one, or several dies) of a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto a target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

Angular-resolved scatterometry for critical dimension (CD) metrology measures the back focal plane diffraction intensity as obtained from dedicated test gratings. Typically multi-parameter shape-profiles of trapezoidal gratings lines are retrieved from the diffraction intensities. Examples of this measurement technique operate at best at a diffraction limit of around 70 nm for the width of a single line (0.25/NA) for UV-light with=280 nm and NA~1. This implies that on-product structures and structured patterns that are typical for hot-spot areas generate intensities only in the 0-th order of diffraction, which is detected within the aperture. These are the so-called propagating waves. Higher-order diffraction intensities only exist within the medium, but are not detectable (and are called the evanescent waves). Still, the 0-th order beam may carry enough information such that by using a-priori knowledge of what structure has been written on the wafer, but the parameters of such a high-frequency structure may be retrieved only up to a certain extent, in particular up to a certain accuracy.

Moreover, information about structures that is beyond the diffraction limit is intrinsically more difficult to be retrieved, and parameters of the diffracting pattern may be highly correlated such that unambiguous and robust reconstruction may be hampered, just because of the fact that the information about the diffracting structure that is present in the back focal plane intensities is just too sparse.

SUMMARY

It is desirable to improve the accuracy and robustness with which high-resolution structures can be measured with scatterometry-based metrology, and hereby extend the application scope of scatterometry-based metrology to high resolutions that were not within reach for this method of metrology.

According to an aspect of the invention, there is provided a scatterometry method measuring a back focal plane diffraction intensity image of a measurement projection system configured to project a radiation beam onto a target portion of a substrate, comprising directing a beam of radiation having a first wavelength to the substrate, providing a diffraction image of a zeroth diffraction order and higher order diffraction from a diffraction structure in the substrate, the diffraction structure comprising a first layer provided with a first structure in a surface area of the substrate, a second layer provided with a periodic structure, wherein a lowest spatial frequency of the periodic structure is lower than the spatial frequencies of interest of the first structure, and determining from the diffraction image originating from diffraction of the radiation beam in both the first and second layer a critical dimension metrology parameter.

According to another aspect of the invention, there is provided a measurement system comprising a scatterometer and a processing system connected to the scatterometer, wherein the scatterometer is arranged to measuring a back focal plane diffraction intensity image of a measurement projection system configured to project a patterned radiation beam onto a target portion of a substrate, by directing a beam of radiation having a first wavelength to the substrate, providing a diffraction image of a zeroth diffraction order and higher order diffraction from a diffraction structure in the substrate, the diffraction structure comprising a first layer provided with a first structure in a surface area of the substrate, a second layer provided with a periodic structure, wherein a lowest spatial frequency of the periodic structure is lower than the spatial frequencies of interest of the first structure, and wherein the processing system is arranged to determine from the diffraction image originating from diffraction of the radiation beam in both the first and second layer a critical dimension metrology parameter.

According to a further aspect of the invention, there is provided a lithographic apparatus arranged to transfer a pattern from a patterning device onto a substrate, wherein the lithographic apparatus comprises such a measurement system.

According to an aspect of the invention, there is provided a device manufacturing method comprising transferring a pattern from a patterning device onto a substrate, wherein the method comprises directing a beam of radiation having a first wavelength to the substrate, providing a diffraction image of a zeroth and higher order diffraction from a diffraction structure in the substrate, the diffraction structure comprising a first layer provided with a first structure in a surface area of the substrate, a second layer provided with a periodic structure, wherein the lowest spatial frequency of the periodic structure is lower than the spatial frequencies of interest of the first structure, and determining from the diffraction image originating from diffraction of the radiation beam in both the first and second layer a critical dimension metrology parameter.

According to a yet another aspect of the invention, there is provided a computer program product comprising computer executable code, which when downloaded on a processing system interfacing with a measurement system according to the present invention, provides the processing system with the functionality of the method according to the present invention.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

Embodiments of the invention will now be described, by way of example only, with reference to the accompanying schematic drawings in which corresponding reference symbols indicate corresponding parts, and in which.

One or more embodiments of the present invention will now be described with reference to the accompanying drawings. In the drawings, like reference numbers can indicate identical or functionally similar elements.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Figure 1:
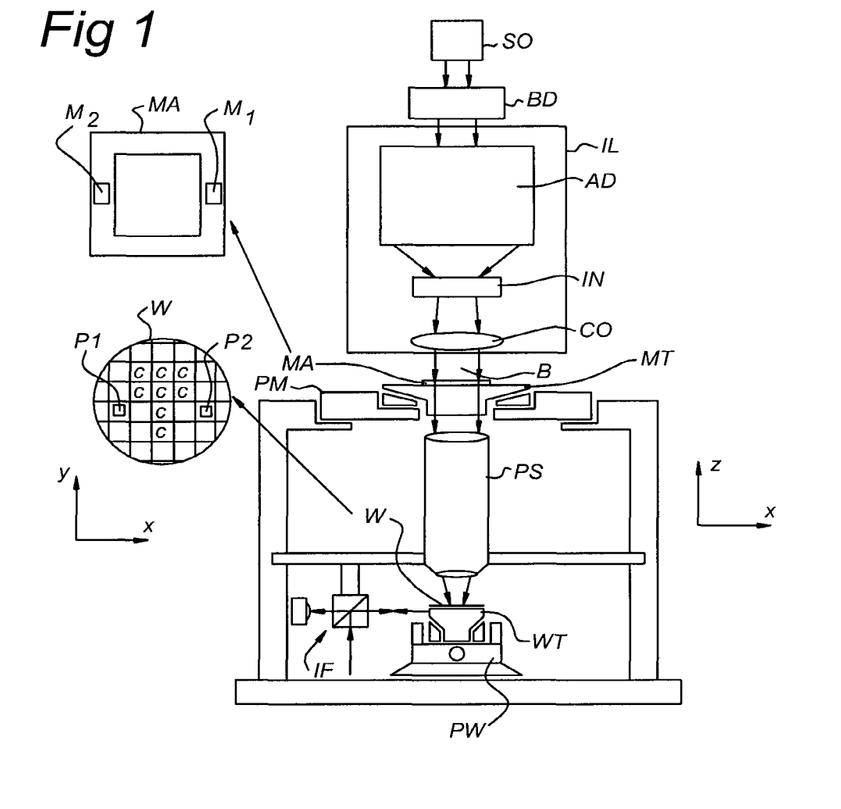
FIG. 1 depicts a lithographic apparatus according to an embodiment of the invention.

FIG. 1 schematically depicts a lithographic apparatus according to one embodiment of the invention. The apparatus comprises an illumination system (illuminator) IL configured to condition a radiation beam B (e.g., UV radiation or DUV radiation). A support structure (e.g., a mask table) MT is constructed and arranged to support a patterning device (e.g., a mask) MA and is connected to a first positioner PM configured to accurately position the patterning device in accordance with certain parameters. A substrate table (e.g., a wafer table) WT is constructed and arranged to hold a substrate (e.g., a resist coated wafer) W and is connected to a second positioner PW configured to accurately position the substrate in accordance with certain parameters. A projection system (e.g., a refractive projection lens system) PS is configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein is intended to be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein is intended to be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as being synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

In the FIG. 1 embodiment, the illuminator IL receives a radiation beam from a radiation source SO. The source and the lithographic apparatus may be separate entities. For example the source may be an excimer laser external to the lithographic apparatus. In such cases, the source is not considered to form part of the lithographic apparatus and the radiation beam transmits from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a "radiation system."

The illuminator IL may comprise an adjuster AD for adjusting the angular intensity distribution of the radiation beam. Generally, at least the outer and/or inner radial extent (commonly referred to as -outer and -inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross section.

During operation of the lithographic apparatus, the radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as "scribe-lane alignment marks"). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.
2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-) magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.
3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2A:
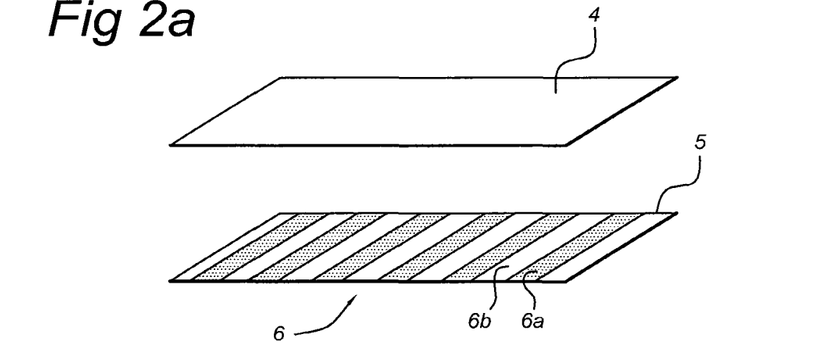
FIG. 2a shows a schematic view of a diffraction structure as used in embodiments of the present invention.
Figure 2B:
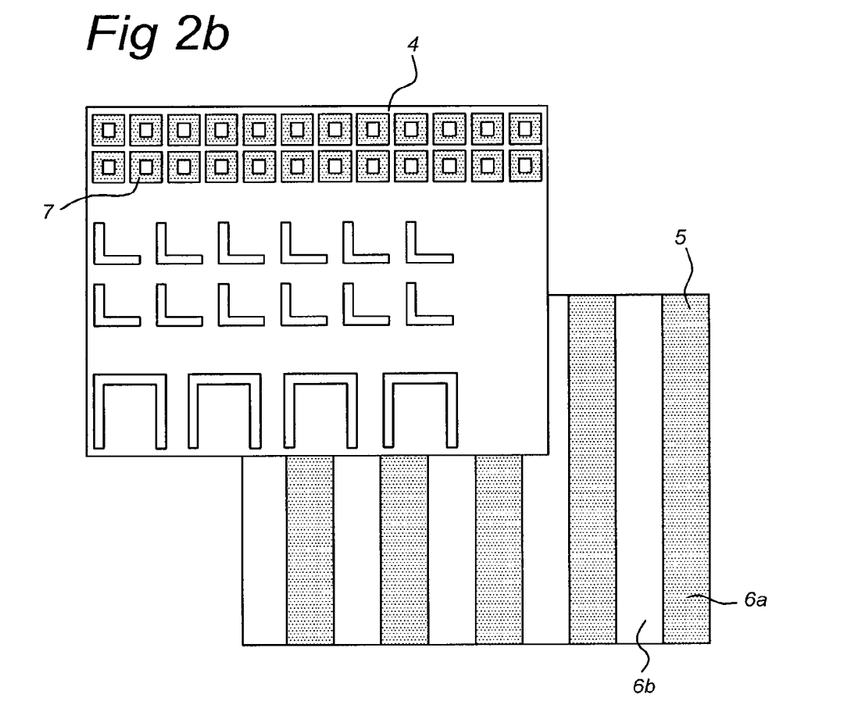
FIG. 2b shows a more detailed view of a top and bottom layer of a diffraction structure as used in embodiments of the present invention.

FIG. 2a shows a schematic view of a diffraction structure as used in embodiments of the present invention. FIG. 2b shows a more detailed view of a top and bottom layer of a diffraction structure as used in embodiments of the present invention. The present invention may include the use of a 3-dimensional diffraction structure that comprises a sandwich stack having at least two layers, and that is positioned at a given location on the substrate W. A first or top layer 4 is provided with a first structure 7, e.g., a one dimensional or two dimensional structure similar to a standard structure to be patterned on the substrate W. Such a first structure 7 usually has very fine structures with small dimensions (high resolution), in other words a spatial frequency content including high frequencies. A second or bottom layer 5 comprises a periodic structure, in the form of a low-frequency 1D or 2D diffraction grating 6, i.e., having a spatial frequency content which is limited to low frequencies.

This specific sandwich-type of diffraction structure may be used for Critical Dimension (CD) reconstruction with improved resolution for the top layer parameters. CD is an important parameter in substrate or wafer W processing, and may be measured using scatterometry measurements of back focal plane diffraction intensity images. In the FIG. 2a embodiment, such a diffraction structure is shown schematically, wherein a bottom layer 5 of a substrate W is provided with a grating 6 having a periodic structure. In this embodiment, the grating is constituted by lines having a line width 6a and grating spaces having a spacing width 6b. The grating has a periodic structure that has a repetition in one direction. Other repetitions are also possible. For example, an alternative grating may have a periodic structure having a repetition (of lines) in two non-parallel directions (e.g., crossing lines).

The lowest spatial frequency of the periodic structure of grating 6 is such that, in at least one case, the difference spatial frequency of a first spatial frequency of the first layer and a second spatial frequency of the second layer falls within the detection aperture of the CD measurement system, so that a signal can be detected from at least double scattering (i.e., diffraction from both the first and second layer 4, 5) with one scattering happening at the first layer 4 and a second scattering happening at the second layer 5.

Figure 5:
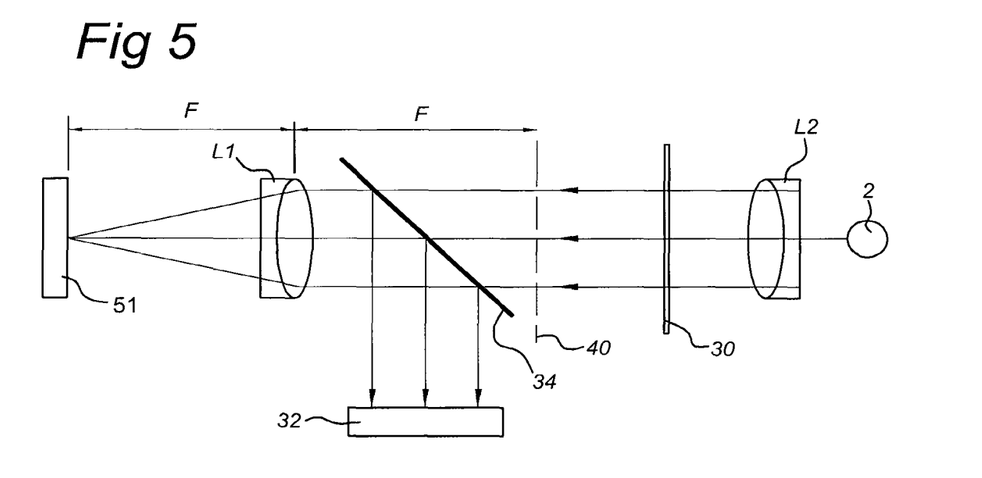
FIG. 5 shows a scatterometry based measurement system as used in the present invention embodiments.

The CD measurement system as used in this description may be any scatterometry based measurement system, e.g., as shown in FIG. 5, which shows a scatterometry based measurement system as used in embodiments of the present invention.

Such a scatterometer 10 is configured to measure a property of a substrate W by measuring, in a pupil plane 40 of a high NA lens, a property of an angle-resolved spectrum reflected from a substrate surface 51 at a plurality of angles and wavelengths. The scatterometer 10 comprises a radiation source 2 configured to project radiation onto the substrate surface 51 and a detector 32 configured to detect reflected spectra. The pupil plane is the plane in which the radial position of radiation defines the angle of incidence, and the angular position defines the azimuth angle of the radiation and any substantially conjugate plane. The detector 32 is placed in the pupil plane of the high NA lens. The NA is high and, in an embodiment, at least 0.9 or at least 0.95. Immersion scatterometers may even have lenses with an NA over 1. A beam from radiation source 2 is focused using lens system L2 through interference filter 30 and is focused onto substrate surface 51 via a microscope objective lens L1 in this embodiment. The radiation is then reflected via partially reflective surface 34 into detector 32, such as, for example, a CCD detector. Detector 32 is positioned in the back projected pupil plane 40 in order to have the scatter spectrum detected. The pupil plane 40 is at the focal length F of the lens system L1. The pupil plane may be re-imaged with auxiliary optics since the pupil plane of a high NA lens is usually located inside the lens. Such a scatterometer is also described in European patent application EP-A-1 628 164, which is incorporated herein by reference in its entirety.

Figure 3:
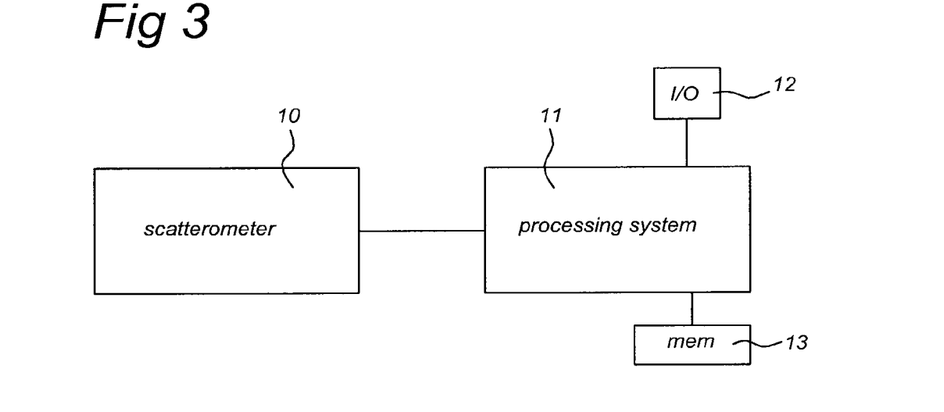
FIG. 3 shows a schematic block diagram of a measurement system according to an embodiment of the present invention.

FIG. 3 shows a schematic block diagram of a measurement system according to an embodiment of the present invention. The scatterometry based measurement system directs a beam of radiation having a first wavelength to the substrate W. As shown in the FIG. 3 embodiment, the CD measurement system may comprise a scatterometer 10 connected to a processing system 11, which controls the scatterometer 10 and processes data generated by the scatterometer 10. The processing system 11 may be implemented as an independent system or as a number of processing units that operate in parallel, wherein each processing unit is arranged to execute sub-tasks of a larger program. The processing units may also be divided in one or more main processing units with several sub processing units. Some processing units of the processing system 11 may even be located a distance away of the other processing units and communicate via a communication network. The processing system 11 may be a computer assembly arranged for loading a computer readable medium comprising computer executable code. This may enable the processing system to execute, when the computer executable code on the computer readable medium is loaded, embodiments of the present methods using scatterometry. The processing system 11 is connected to a memory 13, for storing computer executable instructions and/or to store (intermediate) measurement and other data. Furthermore, the processing system 11 is connected to an input/output interface (I/O) 12, which allows to connect various peripheral systems to the processing system, such as a keyboard/mouse, display, etc.

The present measurement embodiments are implemented in general by modulating high-frequency evanescent waves within the medium that are diffracted by the structure of interest. Referring to FIG. 2b, the diffracting structure is the "first structure" 7 (a grating) in the top layer 4 of the substrate Wb. The modulation process encodes information into propagating waves that are detectable as back focal plane or exit-pupil intensities. The embodiments of the present invention could also be used in phase-retrieval methods of scatterometry. Alternatively, the embodiments of the present invention could also be used in image-based scatterometry.

Modulation is achieved via a diffraction structure of at least two layers 4, 5, thus comprising at least a top layer 4 and a bottom layer 5. For the sake of transparency of the description, examples are described with reference to a two layer sandwich. This is further shown in the schematic view of FIG. 2b.

The top layer 4 is the layer of interest, with which e.g., the critical dimension (CD) metrology parameters of the processing of the substrate W has to be established, and this top layer 4 is provided with the high (spatial) frequency diffracting structure 7 of interest. The first structure 7 as such would only provide a diffraction image having a zeroth order diffraction from the radiation beam. The bottom layer 5 is provided with a simple low-frequency (LF) 1D or 2D diffraction grating 6 that realizes the encoding into the propagating waves. In the FIG. 2b embodiment, a simple one dimensional diffraction grating is shown having lines 6a and spaces 6b of similar width. The wave-fields generated at the top layer 4 propagate further downwards to the bottom layer 5 where they interfere with the structure of the LF grating 6. This interference can be thought of mathematically as the convolution of the top layer wave-front with the limited set of discrete diffraction orders of the LF grating 6. Because of this interference, intrinsic high-frequency information from the top layer 4 gets shifted to inside the detection aperture of the CD measurement system. This interference can be understood as double diffraction, one diffraction event taking place at the first layer 4 and a second diffraction event taking place at a second layer 5, and where the angle of diffraction of the double diffraction event results from the difference of the respective spatial frequencies that dictate the diffraction events in the two respective layers 4, 5. In case the difference of the respective spatial frequency resides within the aperture for detection, the set-up allows to detect high-spatial frequency information of the first layer 4 as encoded lower frequency information because of the difference in frequencies.

In one embodiment, the spatial frequency content of the periodic structure 6 is smaller than a diffraction limit associated with the lens-system of the metrology set-up, characterized by its numerical aperture NA and wavelength, i.e., $0.25*\lambda/NA$, in which $\lambda$ is the wavelength used and NA is the numerical aperture of the objective lens of the metrology/scatterometry set-up.

The back focal plane intensities now carry information about both layers 4, 5, of the diffraction structure, wherein the information content about the high-frequency top layer 4 has increased. Note that for a 1D-grating 6 in the bottom layer 5, the inside-shifting occurs along a single direction only. For a 2D-grating 6 in the bottom layer 5, the inside-shifting occurs along multiple directions in the 2D plane (the directions of the reciprocal lattice of said structure in the bottom-layer 5). A 2D-grating 6 may be provided as a 2D-array of circular/elliptic or square/rectangular structures on a 2D-lattice (square, hexagonal etc.), e.g., a regular array of small rectangles.

According to this embodiment of the present invention, the measurements may be implemented in the processing system 11 (see FIG. 3) using a number of approaches. A first approach is a non-hierarchical approach for CD reconstruction using a sandwich stack 4-5 as described above. In this case, CD-reconstruction aims at retrieval of all parameters for the structures 6 and 7 in both top layer 4 and bottom layer 5 at the same time. Thus, also the parameters of the low frequency 1D or 2D grating 6 are treated as floating parameters that are to be retrieved.

In a second approach, named hierarchical approach for the CD reconstruction of a sandwich stack, first, the parameters relating to the bottom layer 5 are assumed known (by modeling or by actual measurement thereof), and only the parameters relating to the structure 7 of the top layer 4 are considered to be floating. The parameters from the bottom layer 5 are e.g., known from a "standard" CD-reconstruction experiment on the bottom layer 5 only, prior to deposition of the top layer 4. In both the first and second approach, it is assumed that the processing steps for forming the top layer 4 with structure 7 (deposition, etc.) are not influencing the reconstructed parameters of the bottom layer 5.

Further variations in the measurement methods are related to the characteristics of the low (spatial) frequency grating 6 in the bottom layer 5. In a first aspect multiple gratings 6 are provided on a single substrate W (one dimensional or two dimensional gratings), with a different (mutual) orientation. In case of a 1D-grating 6 in the bottom layer 5, the "inside-shifting of information" takes place along one direction only. High-resolution information that resides in the pupil-areas orthogonal to this direction is still unaltered. In order to enable "inside-shifting" of this information, multiple areas on the substrate W are used for scatterometry, each area having the same top layer 4 (and structure 7), whereas the bottom layer 5 comprises a number of 1D gratings 6 that have a different orientation for each of the separate grating 6. An example is a set of only two gratings 6 with the 1D gratings 6 oriented under 90 degrees with respect to each other. A further example would be a set of three different gratings 6, with orientations of 0, 45 and 90 degrees, etc.

In a second aspect, another characteristic parameter of the gratings 6 in the bottom layer 5 is varied between at least two of the gratings 6. This characteristic parameter is e.g., the pitch of the one dimensional or two dimensional pattern of the gratings 6, which varies the amount of "inside-shifting" for a set of different patterns. This knowledge can than be used by the processing system 11 when determining e.g., the CD using the structure 7 in the top layer 4.

In the following, further details are described relating to the reconstruction of the Critical Dimension (CD) pattern of the top layer 4 of the substrate W, using multiple back focal plane intensity measurements (using scatterometer 10) for multiple diffraction structures comprising varying gratings 6 in bottom layer 5. As parameters to be retrieved, the parameters from the structure 7 in the top layer 4 and possibly the parameters of the LF grating 6 in the bottom layer 5 are to be determined. This is dependent on the use of hierarchical or non-hierarchical approaches as explained above. Further, a multitude of patterns may be measured, each of these patterns has the same top layer 4, but the LF-grating 6 in the bottom layer 5 is varied in orientation and/or pitch. The parameters of the top layer 4 may be considered to be common to all of the measured back focal plane images. CD-reconstruction then takes place with as input said multitude of back focal plane images, and as output the set of common parameters of the top layer 4 (in the hierarchical scheme).

Further variations may be implemented as embodiments of the present invention. The order of top layer 4 and bottom layer 5 in the sandwich could be reversed (with the layer of interest at the bottom, and the LF grating 6 at the top). This configuration is less ideal mainly because of two reasons. First because scattering by the bottom layer 5 is weaker than from the top layer 4, because of the absorption of light on its way downwards, and secondly, because then a separate measurement and characterization of the LF grating 6 cannot be done without sacrificing extra real estate on the wafer surface (namely, the LF grating 6 on the top must also be deposited on top of an area without patterned structures in the layers below).

In the above examples, a two layer sandwich is described. In a further embodiment, a three layer sandwich where the center layer and bottom layer 5 are provided with low frequency 1D-gratings, such as, for example, grating 6 in layer 5, at for instance different (e.g., orthogonal) orientations. In such case, "inside-shifting" takes place simultaneously along these two (orthogonal) directions.

In the above examples, simple low frequency gratings 6 as structures in the bottom layer 5 (one or two dimensional gratings 6) with the main purpose to realize the "inside-shifting" of the high-resolution information related to the structure 7 of the top layer 4 have been used. In principle, any pattern 6 with a known low (spatial) frequency content could be used.

In all of the embodiments described so far, it is assumed that the different patterns 6, 7 are generated close to each other on the substrate W, allowing to assume that inter-pattern variation of the parameters is negligible. In other words the patterns 6, 7 must be the same apart from the intended variations in orientation and pitch of the low frequency grating 6 in the bottom layer 5.

EXAMPLE

Figure 4:
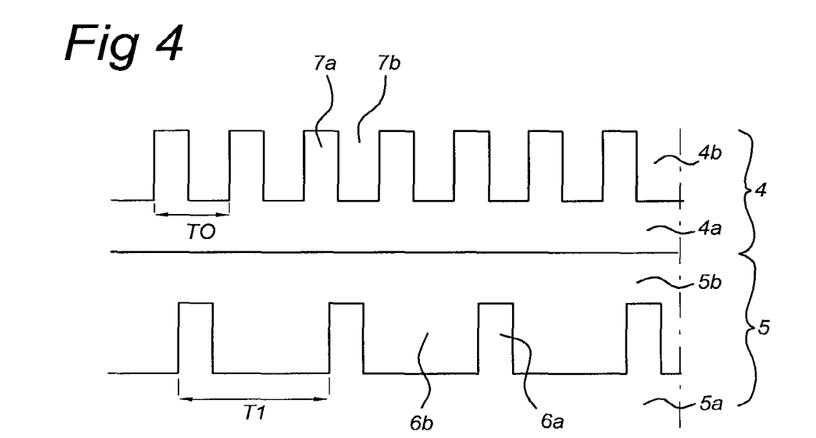
FIG. 4 shows a cross sectional view of an exemplary diffraction structure as used in present invention embodiments.

In the FIG. 4 embodiment, an example is shown of a two layer sandwich structure on a substrate W. The bottom layer 5 comprises a bottom part 5*a* having a low frequency grating 6 with Si lines 6*a*. The bottom layer 5 further comprises a bottom anti-reflective coating 5*b*, forming the spaces 6*b* of the low frequency grating 6. The top layer 4 comprises a resist layer 4*a*, in which lines 7*a* are being formed (with a high spatial frequency), and an air layer 4*b*, which form the spaces 7*b* of the structure 7. The first pitch T0 of the structure 7 (including the widths of portions 7*a* and 7*b*) is shown, as well as the second pitch T1 of the low frequency grating 6. In order to limit possible difficulties in processing of data obtained by scatterometer 10, the first and second pitches T0 and T1 are commensurate, i.e., $m*T1=n*T0$, m and n being integer values.

The above described embodiments of the present invention all allow access to high-resolution information of metrology patterns (in the top layer 4) without the use of shorter wavelengths in the scatterometer 10. By using a diversity in pattern information (originating from multiple patterns e.g., with respect to orientation and (2D) pitch, as low frequency grating 6) as input for CD-Reconstruction of a top layer 4 of interest, a very robust and efficient measurement system is provided.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

CONCLUSION

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections can set forth one or more, but not all exemplary embodiments of the present invention as contemplated by the inventor(s), and thus, are not intended to limit the present invention and the appended claims in any way.

What is claimed is:

1. A scatterometry method for measuring a diffraction intensity image of a measurement projection system, the method comprising:
    directing a beam of radiation having a first wavelength to a substrate;
    detecting the diffraction intensity image from a diffraction structure in the substrate, the diffraction structure comprising:
        a first layer having a first structure with a first spatial frequency in a surface area of the substrate;
        a second layer having a periodic structure having a second spatial frequency,
        wherein the second spatial frequency of the periodic structure is lower than the first spatial frequency of the first structure; and
    determining critical dimension data from the diffraction intensity image originating from diffraction of the beam of radiation in both the first and second layers dimension.

2. The scatterometry method of claim 1, wherein the second spatial frequency is smaller than a diffraction limit associated with the measurement projection system.

3. The scatterometry method of claim 1, wherein the periodic structure of the second layer is a structure with a repetition in one direction.

4. The scatterometry method of claim 1, wherein the periodic structure of the second layer is a structure with a repetition in two non-parallel directions.

5. The scatterometry method of claim 1, further comprising:
    obtaining the critical dimension data related to the first layer and the second layer based on the same beam of radiation.

6. The scatterometry method of claim 1, further comprising:
    obtaining the critical dimension data related to the second layer by measuring a sample with the second layer prior to deposition of the first layer on the substrate; and
    obtaining the critical dimension data related to the first layer using measured data of the second layer.

7. The scatterometry method of claim 1, wherein the diffraction structure comprises a plurality of periodic structures in the second layer, the plurality of periodic structures each having a different orientation.

8. The scatterometry method of claim 1, wherein the diffraction structure comprises a plurality of periodic structures in the second layer, the plurality of periodic structures each having different pitch characteristics.

9. The scatterometry method of claim 1, wherein the first layer is a top layer of the substrate.

10. The scatterometry method of claim 1, wherein the first layer is a bottom layer of the substrate.

11. The scatterometry method of claim 1, wherein:
    the first structure is a pattern with a first pitch T0;
    the periodic structure is a pattern with a second pitch T1; and
    $m*T1=n*T0$, wherein m and n are integers.

12. A measurement system, comprising:
    a scatterometer configured to:
        direct a beam of radiation having a first wavelength to a substrate;
        detect a diffraction image from a diffraction structure in the substrate, the diffraction structure comprising:

a first layer having a first structure with a first spatial frequency in a surface area of the substrate; and a second layer having a periodic structure having a second spatial frequency, wherein the second spatial frequency of the periodic structure is lower than the first spatial frequency of the first structure; and a processing system coupled to the scatterometer, the processing system configured to determine critical dimension data from the diffraction intensity image originating from diffraction of the beam of radiation in both the first and second layer.

13. A lithographic apparatus arranged to transfer a pattern from a patterning device onto a substrate comprising a measurement system according to claim 12.

14. A device manufacturing method comprising:

directing a beam of radiation having a first wavelength to a substrate;

detecting a diffraction image from a diffraction structure in the substrate, the diffraction structure comprising:

a first layer having a first structure with a first spatial frequency in a surface area of the substrate, and a second layer having a periodic structure having a second spatial frequency, wherein the second spatial frequency of the periodic structure is lower than the first spatial frequency of the first structure; and determining critical dimension data from the diffraction image originating from diffraction of the radiation beam in both the first and second layer.

15. A non-transitory computer readable medium having stored thereon computer executable instructions that, in response to execution by a processing system, cause the processing system to perform operations comprising:

directing a beam of radiation having a first wavelength to a substrate;

detecting a diffraction image from a diffraction structure in the substrate, the diffraction structure comprising:

a first layer having a first structure with a first spatial frequency in a surface area of the substrate, and a second layer having a periodic structure having a second spatial frequency, wherein the second spatial frequency of the periodic structure is lower than the first spatial frequency of the first structure; and determining critical dimension data from the diffraction image originating from diffraction of the beam of radiation in both the first and second layers.

16. The non-transitory computer readable medium of claim 15, further comprising:

obtaining the critical dimension data related to the first layer and the second layer based on the same beam of radiation.

17. The scatterometry method of claim 1, wherein the first spatial frequency is greater than a diffraction limit associated with the measurement projection system.

18. The scatterometry method of claim 1, wherein the diffraction intensity image comprises a back focal plane diffraction intensity image.

19. The scatterometry method of claim 1, wherein a difference between the second spatial frequency of the periodic structure and the first spatial frequency of the first structure results in a difference spatial frequency that is detectable by the measurement projection system.

20. The scatterometry method of claim 1, wherein the diffraction structure further comprises:

a third layer having a second periodic structure having a third spatial frequency, wherein the second periodic structure is configured at a different orientation from the periodic structure of the second layer, and wherein the third spatial frequency is lower than the first spatial frequency of the first structure.

* * * * *

UNITED STATES PATENT AND TRADEMARK OFFICE
CERTIFICATE OF CORRECTION

PATENT NO. : 8,520,212 B2
APPLICATION NO. : 13/000212
DATED : August 27, 2013
INVENTOR(S) : Coene et al.

Page 1 of 1

It is certified that error appears in the above-identified patent and that said Letters Patent is hereby corrected as shown below:

In the Claims

Column 12,

Claim 11, line 58, please delete "TO" and replace with "T0"

Claim 11, line 61, please delete "m * Tl = n* TO" and replace with "m * Tl = n * T0"

Signed and Sealed this
Seventeenth Day of December, 2013

Margaret A. Focarino
*Commissioner for Patents of the United States Patent and Trademark Office*